United States Patent
Yokota (10) Patent No.: US 11,291,800 B2
(45) Date of Patent: Apr. 5, 2022

(54) CATHETER BODY AND HUB SECURING APPARATUS

(71) Applicant: TERUMO KABUSHIKI KAISHA, Tokyo (JP)

(72) Inventor: Takayuki Yokota, Chuo (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 147 days.

(21) Appl. No.: 16/534,819

(22) Filed: Aug. 7, 2019

(65) Prior Publication Data
US 2019/0358433 A1 Nov. 28, 2019

Related U.S. Application Data

(63) Continuation of application No. PCT/JP2018/010384, filed on Mar. 16, 2018.

(30) Foreign Application Priority Data

Mar. 17, 2017 (JP) .............................. JP2017-053202

(51) Int. Cl.
*A61M 25/00* (2006.01)
*A61M 39/10* (2006.01)

(52) U.S. Cl.
CPC .... *A61M 25/0097* (2013.01); *A61M 39/1011* (2013.01)

(58) Field of Classification Search
CPC .......... A61M 25/0097; A61M 25/0014; A61M 25/0606; A61M 5/34; A61M 5/343; A61M 5/344
See application file for complete search history.

(56) References Cited

U.S. PATENT DOCUMENTS

| | | | |
|---|---|---|---|
| 2007/0005001 A1* | 1/2007 | Rowe | A61M 25/0014 604/19 |
| 2011/0319825 A1* | 12/2011 | Goral | A61M 25/0102 604/164.01 |

FOREIGN PATENT DOCUMENTS

| | | |
|---|---|---|
| EP | 0502714 A1 | 9/1992 |
| JP | 58-133348 | 9/1983 |
| JP | H06-125989 A | 5/1994 |
| JP | 2009-207611 A | 9/2009 |

(Continued)

OTHER PUBLICATIONS

International Preliminary Report on Patentability for International Application No. PCT/JP2018/010384, dated Sep. 26, 2019.

(Continued)

*Primary Examiner* — Bhisma Mehta
*Assistant Examiner* — Neeraja Gollamudi
(74) *Attorney, Agent, or Firm* — Thaine Lennox-Gentle; Sheridan Ross, PC (57) ABSTRACT

A catheter is provided that includes a catheter body, a catheter hub, and a securing member disposed in the catheter hub to clamp the catheter between the securing member and the catheter hub. The securing member has an outer peripheral surface making contact with and stretching an inner peripheral surface of the catheter body. The catheter includes a recessed relief portion into which a thickness of the catheter body is inserted, the relief portion being partially provided circumferentially in an inner peripheral surface of the catheter hub.

20 Claims, 7 Drawing Sheets

(56) References Cited

FOREIGN PATENT DOCUMENTS

JP         2009207611 A  *  9/2009
JP         2009-268727 A    11/2009

OTHER PUBLICATIONS

International Search Report for International Application No. PCT/JP2018/010384, dated May 22, 2018.
Written Opinion for International Application No. PCT/JP2018/010384, dated May 22, 2018.

* cited by examiner

CATHETER BODY AND HUB SECURING APPARATUS

CROSS REFERENCE TO RELATED APPLICATIONS

The present application is a continuation of and claims benefit to PCT Application No. PCT/JP2018/010384, filed on Mar. 16, 2018, entitled "Catheter" which claims priority to Japanese Patent Application No. 2017-053202, filed on Mar. 17, 2017. The entire disclosures of the applications listed above are hereby incorporated herein by reference, in their entirety, for all that they teach and for all purposes.

FIELD

The present disclosure is generally directed to a catheter including a catheter body and a catheter hub which are secured to each other.

BACKGROUND

A catheter includes a catheter body and a catheter hub fixedly retaining the catheter body and is used as an introducing portion for infusion or transfusion. In order to secure the catheter body to the catheter hub, for example, a sleeve (securing member) may be used as disclosed in Japanese Patent Application JP H06-125989. The sleeve is inserted into the catheter hub to secure the catheter body between the outer peripheral surface of the sleeve and the inner peripheral surface of the catheter hub.

SUMMARY

Incidentally, although the catheter body is designed to have an appropriate thickness to be held between the catheter hub and the securing member, the thickness of the catheter body may change from a designed dimension due to a factor, such as a manufacturing error or the like during manufacture. In particular, when a thickness of the catheter increases, the catheter hub or securing member receives a large repulsive load from the catheter, causing an inconvenience, such as breakage of the catheter hub or impossible assembly between the catheter and the catheter hub.

The present solves these problems, and it is an object of the present disclosure to provide a catheter capable of satisfactorily securing a catheter body to a catheter hub by suppressing the influence of a change in thickness of a catheter body with a material accommodating structure.

In some embodiments of the present disclosure a catheter is described that includes a catheter body, a hollow catheter hub configured to receive insertion of the catheter body, a securing member disposed in the catheter hub to hold the catheter body between the securing member and the catheter hub, the securing member having an outer peripheral surface making a close contact with an inner peripheral surface of the catheter body, and a recessed relief portion into which a thickness of the catheter body enters, the relief portion being partially provided circumferentially at least in one of an inner peripheral surface of the catheter hub and an outer peripheral surface of the securing member.

According to the embodiments described herein, the catheter may have an arrangement in which the relief portion is partially provided circumferentially at least in one of the inner peripheral surface of the catheter hub and the outer peripheral surface of the securing member, and this arrangement suppresses the influence of an increase in the thickness of the catheter body. That is, even when a thickness of the catheter body is large, the thickness of the catheter body being held between the catheter hub and the securing member is deformed (inserted) into the relief portion, reducing a repulsive load applied from the catheter body on the catheter hub or securing member. Furthermore, the inner peripheral surface of the catheter hub and the outer peripheral surface of the securing member may have a portion with no relief portion, the portion exerts a strong compressive force on the catheter body. Therefore, the securing member satisfactorily secures the catheter body and the catheter hub together forming the catheter.

In some embodiments, the relief portion may comprise a groove portion cut out to extend in the axial direction of the catheter hub.

The catheter may be configured so that the relief portion having the groove portion enables smooth insertion of the catheter body and/or the securing member along the groove portion of the catheter hub when being assembled and the thickness of the catheter body is caused to satisfactorily move to (e.g., displace into) the relief portion during the insertion.

Additionally or alternatively, a plurality of the groove portions may be arranged circumferentially surrounding the axis of the catheter body.

In the catheter, the plurality of groove portions surrounding the axis of the catheter body accommodates a portion of the thickness of the catheter body to an appropriate groove portion, equalizing a repulsive load. Stated another way, a portion of material disposed at the end of the catheter body may be caused to displace or deform into the plurality of groove portions when the catheter body and the securing member are inserted into the catheter hub. Without this plurality of groove portions, the portion of material trapped or clamped between a catheter hub and a securing member would be unable to significantly move in a radial direction (e.g., perpendicular to the axis of the catheter body, etc.). As such, compression of the portion of material between the catheter hub and the securing member would exert a repulsive force between the catheter hub and the securing member causing an increase of stress in the joint of the catheter (e.g., in the area of the catheter where the catheter hub, the securing member, and the catheter body are connected, etc.). However, providing the plurality of groove portions into which the portion of material may be displaced (e.g., allowing the portion of material to move in a radial direction when compressed), among other things, reduces the repulsive force between the catheter hub and the securing member and decreases the overall stress in the joint of the catheter when compared to a joint that does not include the groove portion and/or relief portion described herein. Furthermore, even when the catheter body has a circumferentially non-uniform thickness, the thickness of the catheter body can easily displace or deform into any of the groove portions.

The inner peripheral surface of the catheter hub includes a distal inner peripheral surface having a continuous constant inner diameter and a tapered inner peripheral surface extending from a proximal end of the distal inner peripheral surface and having an inner diameter gradually increasing proximally, the outer peripheral surface of the securing member includes a distal outer peripheral surface facing the distal inner peripheral surface and a tapered outer peripheral surface facing the tapered inner peripheral surface, and the relief portion is preferably provided across an inner peripheral surface boundary portion between the distal inner peripheral surface and the tapered inner peripheral surface or an outer peripheral surface boundary portion between the distal outer peripheral surface and the tapered outer peripheral surface.

Since the inner peripheral surface boundary portion and/or the outer peripheral surface boundary portion bends, or otherwise deforms, the catheter body into a tapered shape, the thickness of the catheter body tends to increase. Therefore, a securing mechanism has a configuration in which the relief portion provided across the inner peripheral surface boundary portion and/or the outer peripheral surface boundary portion accommodates the thickness of the catheter body at this position well.

In one embodiment, the relief portion is provided in the inner peripheral surface of the catheter hub, and a distal end of the relief portion is located proximally from a distal end of the securing member.

Thus, the securing mechanism deforms a portion of the thickness of the catheter body into the groove portion near the inner peripheral surface boundary portion and/or the outer peripheral surface boundary portion and, at the same time, sufficiently tightly holds the catheter body at a position disposed distally from the relief portion.

Alternatively, the relief portion may be provided in the inner peripheral surface of the catheter hub, and the distal end of the relief portion may be located distally from the distal end of the securing member.

Thus, the compressive force exerted on the catheter body is suppressed on the distal end side of the securing member, in cooperation with the catheter hub, and during assembly, the catheter body can be smoothly inserted into the catheter hub (e.g., allowing material of the catheter body to deform at least partially into the relief portion).

In addition, for example, the relief portion may be provided in the inner peripheral surface of the catheter hub, and a proximal end of the relief portion may be located proximally from a proximal end of the catheter body.

Thus, in manufacturing the catheter, the thickness of the catheter body near an end portion, which is easily changed, is reliably and readily accommodated by and disposed in the relief portion.

In some embodiments, the relief portion may be provided in the outer peripheral surface of the securing member, and a distal end of the relief portion may be provided proximally from a distal end of the distal outer peripheral surface, and the proximal end of the relief portion may be provided distally from a proximal end of the tapered outer peripheral surface.

The relief portion provided in the outer peripheral surface of the securing member simplifies manufacture of the catheter. Furthermore, the relief portion is not provided at the distal end and the proximal end, and thereby the securing member obtains sufficient strength.

Still furthermore, in the inner peripheral surface of the catheter hub and/or the outer peripheral surface of the securing member, a protruding portion protruding in a direction opposite to the relief portion may be formed at a position circumferentially adjacent to the relief portion.

The catheter has the relief portion and the protruding portion, and a portion to which a strong compressive, or clamping, force is exerted on the catheter body and a portion from which the thickness of the catheter body can expand and is accommodated are formed to be divided circumferentially.

According to embodiments of the present disclosure, it is possible for the catheter to secure the catheter body and the catheter hub by suppressing the influence of a change in thickness of the catheter body with the arrangements described herein.

DETAILED DESCRIPTION

Embodiments of a catheter according to the present disclosure will be described below in detail with reference to the accompanying drawings.

Figure 1:
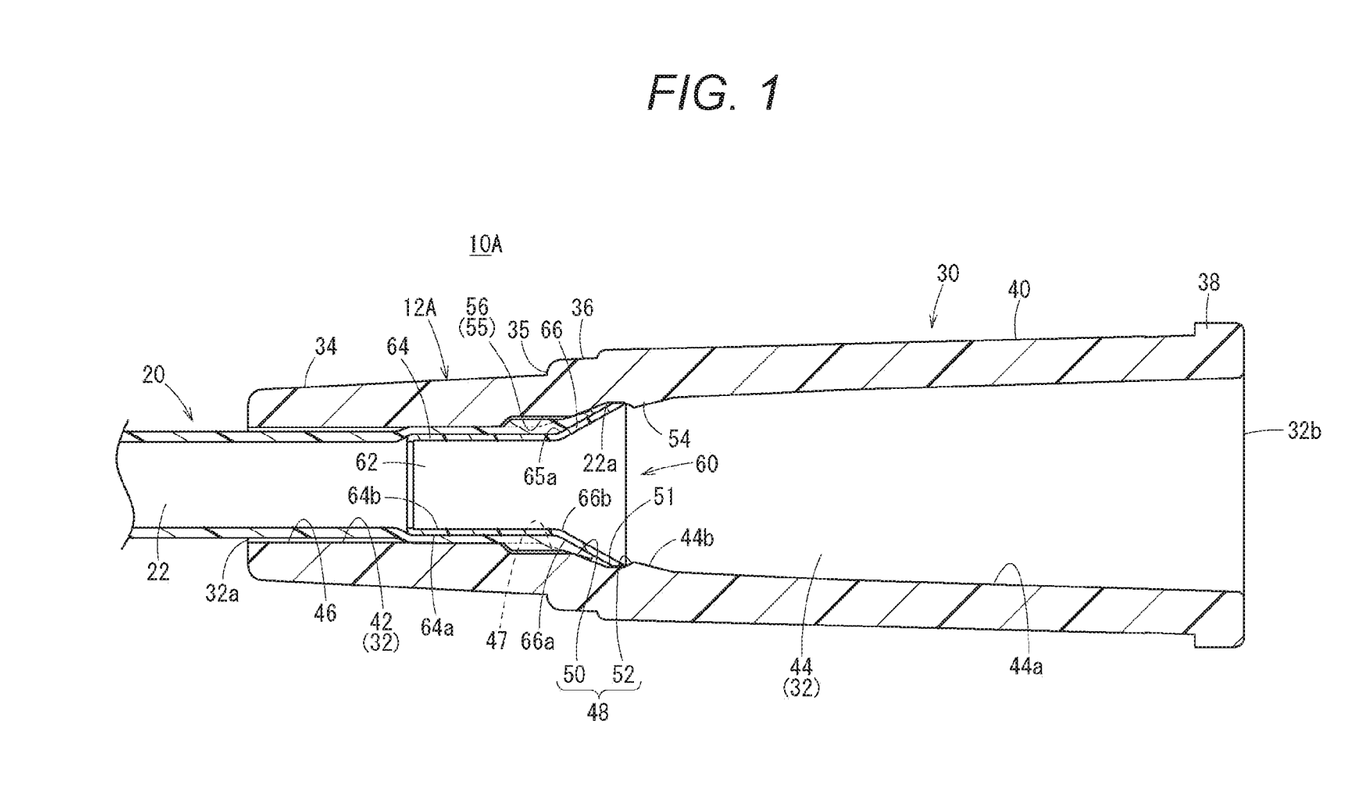
FIG. 1 is a cross-sectional side view of a catheter in accordance with an embodiment of the present disclosure.

In one embodiment, a catheter 10A may include a medical device comprising an introducing portion for infusion or transfusion to a patient (living body) or a deriving portion for blood upon blood sampling. As illustrated in FIG. 1, the catheter 10A includes a catheter body 20 configured to be inserted into a body of the patient, and a hollow catheter hub 30 configured to fixedly retain a proximal end side of the catheter body 20 to be placed in the patient together with the catheter body 20.

In some embodiments, the catheter 10A may be a so-called peripheral venous catheter (PVC), where the catheter body 20 is relatively short (e.g., shorter than a central venous catheter, etc.) to be placed in a peripheral vein. In any event, the catheter 10A may employ, for example, a central venous catheter, a PICC, a midline catheter or the like having a length longer than that of the PVC. Furthermore, the catheter 10A may have an arterial catheter, such as a peripheral arterial catheter, in addition to the intravenous catheter.

Before use, the catheter 10A may be assembled to a catheter assembly (not illustrated) configured to insert and indwell the catheter body 20 into the body. The catheter assembly may include an inner needle and an inner needle hub, and in a state before use (e.g., a state before puncture), the inner needle may be inserted through a lumen 22 of the catheter body 20, and a tip of the inner needle may be exposed from a distal end of the catheter body 20, forming a multi-layered needle. Furthermore, the inner needle hub fixedly retains a proximal end side of the inner needle to constitute a grip portion gripped by a user, such as a doctor or a nurse, and the catheter hub 30 may have a proximal end portion removably mounted to a distal end portion of the inner needle hub. That is, the catheter assembly is configured to integrally operate the catheter 10A (e.g., the catheter body 20, the catheter hub 30, etc.), the inner needle, and the inner needle hub in the state before puncture.

In use, the user inserts the multi-layered needle to make a puncture in the body of the patient so that the tip of the inner needle and the distal end of the catheter body 20 reach a blood vessel. Then, the user operates the catheter hub 30 to advance while maintaining the puncture state so that the catheter hub 30 disengages from the inner needle hub, and further causes the catheter body 20 and the catheter hub 30 to advance relative to the inner needle. Accordingly, after the catheter body 20 is inserted into the blood vessel, the inner needle and the inner needle hub are retracted relative to the catheter body 20 and the catheter hub 30 and withdrawn from the catheter hub 30, indwelling the catheter 10A in the patient. Hereinafter, the catheter 10A will be described in detail.

The catheter body 20 of the catheter 10A is a flexible linear tubular member, and the lumen 22 axially extending therethrough is provided inside the catheter body 20. The catheter body 20 is formed to have a constant outer diameter and an inner diameter in an axial direction of the catheter body 20 by a manufacturing method, such as extrusion molding or heating a heat shrinkable tube.

The lumen 22 of the catheter body 20 communicates with a distal end opening (not illustrated) defined at the distal end of the catheter body 20 and a proximal end opening 22a defined at the proximal end of the catheter body 20. The lumen 22 can house the inner needle in the state before puncture and functions as a flow path for making medicine or blood to flow therethrough in a state where the catheter body 20 is indwelled in a blood vessel.

The catheter body 20 preferably has a shape (axial length, thickness, or the like) and physical property (flexibility, rigidity, or the like) which are appropriately designed to insert and indwell the catheter body 20 in the blood vessel satisfactorily. For example, the catheter body 20 preferably has an axial length within the range of 10 mm to 70 mm. Furthermore, for example, the catheter body 20 preferably has an outer diameter within the range of 0.5 mm to 2.5 mm and an inner diameter (a diameter of the lumen 22) within the range of 0.3 mm to 2.0 mm.

The thickness of the catheter body 20 (e.g., the wall thickness of the catheter body 20 measured as a distance between the inner diameter and the outer diameter) affects the physical properties of the catheter body 20 together with a constituent material, and the thickness is preferably formed into an appropriate dimension. For example, the thickness of the catheter body 20 is preferably within the range of 0.06 mm to 0.3 mm. Examples of the constituent material of the catheter body 20 include, but are not particularly limited to, a fluorine-based resin, such as polytetrafluoroethylene (PTFE), ethylene tetrafluoroethylene (ETFE) copolymer, and perfluoroalkoxy (PFA), an olefin-based resin, such as polyethylene and polypropylene or a mixture thereof, polyurethane, polyester, polyamide, polyether-nylon resin, a mixture of the olefin-based resin and an ethylene-vinyl acetate copolymer, and the like.

Furthermore, since the catheter body 20 is made of a transparent resin material, it is possible to cause the user to visually confirm blood (e.g., flashback) flowing between an inner peripheral surface of the catheter body 20 and an outer peripheral surface of the inner needle upon inserting the multi-layered needle to make a puncture. The catheter body 20 is not limited to the above configuration and may adapt various configurations. For example, a physical property of the catheter body 20 may be changed by changing the thickness (e.g., by changing at least one of the outer diameter and the inner diameter of the catheter body 20) thereof along the axial direction. Furthermore, a flexible resin material different from that of a main body portion of the catheter body 20 may be applied to the distal end of the catheter body 20.

On the other hand, the catheter hub 30 may be formed as a hollow substantially cylindrical shape, which may comprise a material that is harder than the catheter body 20 and larger than the catheter body 20 in outer diameter, and an internal space 32 communicating with the lumen 22 of the catheter body 20 is provided inside the catheter hub 30. The internal space 32 communicates with the distal end opening 32a defined at the distal end of the catheter hub 30 and a proximal end opening 32b defined at the proximal end of the catheter hub 30. The catheter hub 30 firmly secures the catheter body 20 by inserting the catheter body 20 from the proximal end opening 32b. Into the catheter hub 30, a plug of a tube for infusion, transfusion, or blood sampling may be inserted from the proximal end opening 32b and removably secured.

An outer peripheral surface of the catheter hub 30 is tapered stepwise distally. Specifically, the catheter hub 30 includes a stepped portion 35 near the distal end relative to an axially intermediate position, and the catheter hub 30 further includes a distal outer peripheral surface 34 on the distal end side, and a proximal outer peripheral surface 36 on the proximal end side, with the stepped portion 35 as a base point. An outer diameter of the distal outer peripheral surface 34 is smaller than an outer diameter of the proximal outer peripheral surface 36 and gradually decreases toward the distal end. Similarly, the outer diameter of the proximal outer peripheral surface 36 also gradually decreases from the proximal end toward the stepped portion 35.

The proximal end of the proximal outer peripheral surface 36 is provided with a flange portion 38 projecting radially outward. Furthermore, the proximal outer peripheral surface 36 is provided with a ridge portion 40 projecting radially outward with a small height and distally extending toward the flange portion 38. A plurality of the ridge portions 40 is provided in a circumferential direction of the catheter hub 30 to increase the rigidity of the catheter hub 30.

The internal space 32 of the catheter hub 30 includes a distal space 42 defined to secure the catheter body 20, and a proximal space 44 extending from a proximal end side of the distal space 42 and having a volume larger than that of the distal space 42.

The proximal space 44 is opened through the proximal end opening 32b of the catheter hub 30, and the plug of the tube is inserted therefrom as described above. The proximal space 44 may store, for example, a hemostasis valve, which is not illustrated, configured to prevent flowing out of blood flowing through the lumen 22 upon puncture of the inner needle, and a plug, which is not illustrated, penetrating the hemostasis valve by insertion of the plug of the tube, enabling infusion.

More specifically, an inner peripheral surface of the proximal space 44 may include a Luer tapered surface 44a having an inner diameter gradually decreasing distally, and a drawn surface 44b extending from the distal end of the Luer tapered surface 44a and having an inner diameter sharply decreasing distally relative to that of the Luer tapered surface 44a. The Luer tapered surface 44a is fitted to the plug inserted into the proximal space 44 with an appropriate fitting force.

On the other hand, in the distal space 42, in addition to a proximal end portion of the catheter body 20, the securing member 60 is inserted and housed. That is, in the catheter 10A, the inner peripheral surface of the catheter hub 30 and the outer peripheral surface of the securing member 60 constitutes a securing mechanism 12A to hold or clamp the catheter body 20 therebetween, and the catheter body 20 is secured.

Figure 2A:
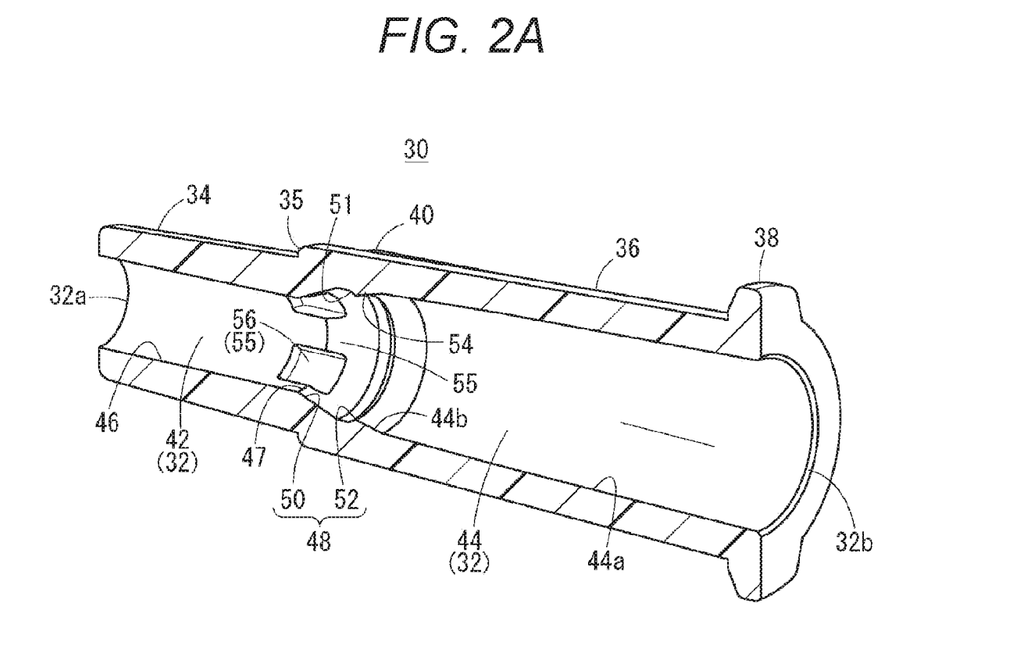
FIG. 2A is a perspective cross-sectional view of a catheter hub of the catheter of FIG. 1.

Specifically, as illustrated in FIG. 2A, the distal space 42 has an inner peripheral surface which includes a distal inner peripheral surface 46 defining the distal end opening 32a at the distal end and having a predetermined axial length, and a recessed inner peripheral surface 48 extending from the proximal end of the distal inner peripheral surface 46 and formed within the range of a length axially smaller than that of the distal inner peripheral surface 46.

The distal inner peripheral surface 46 extends with a substantially constant diameter in the axial direction and is provided at a position overlapping the distal outer peripheral surface 34 in the axial direction of the catheter hub 30. The recessed inner peripheral surface 48 is provided at a position overlapping the position of a distal end of the proximal outer peripheral surface 36 in the axial direction of the catheter hub 30. Since the catheter hub 30 includes the recessed inner peripheral surface 48 on the proximal end side of a position where the stepped portion 35 is formed, the catheter hub 30 has a side cross-section having a shape axially extending without a large change in thickness.

Furthermore, the recessed inner peripheral surface 48 includes a distal tapered inner peripheral surface 50 having a diameter gradually decreasing distally, and a proximal tapered inner peripheral surface 52 having a diameter sharply decreasing proximally relative to that of the distal tapered inner peripheral surface 50, with a bottom portion 51 located on the radially outermost side as a base point. The proximal tapered inner peripheral surface 52 extends from a distal end of the drawn surface 44b of the proximal space 44. That is, the drawn surface 44b and the proximal tapered inner peripheral surface 52 constitute a projection portion 54, or ridge, in which the thickness of the catheter hub 30 projects inward toward a center axis of the catheter hub.

The catheter hub 30 includes a groove portion 56 (e.g., a relief portion 55) having a recessed shape and axially extending a short distance at an inner peripheral surface boundary portion 47 between the distal inner peripheral surface 46 and the recessed inner peripheral surface 48. A plurality of these groove portions 56 are provided in a circumferential direction of the catheter hub 30. In one embodiment, four groove portions 56 may be provided circumferentially surrounding the axis of the catheter body 20. A distal end of each of the groove portions 56 may be located in a portion of the distal inner peripheral surface 46 separated a distance distally apart from the inner peripheral surface boundary portion 47, while a proximal end of the groove portion 56 may be located near the inner peripheral surface boundary portion 47 (in the distal tapered inner peripheral surface 50 slightly rearward from the inner peripheral surface boundary portion 47).

The groove portion 56 is formed shallow by being cut out (thickness reduction) radially outwardly with the distal inner peripheral surface 46 as a reference surface and extends at a constant depth in the axial direction of the catheter hub 30. Each groove portion 56 has a circumferential width set, for example, at around ⅛ (or slightly wider than ⅛) of a circumferential length of the catheter hub 30. A portion between two adjacent groove portions 56 is a remaining portion of the distal inner peripheral surface 46 and the distal tapered inner peripheral surface 50, and this portion may be referred to as a protrusion 58 protruding radially outward relative to an adjacent groove portion 56.

Figure 2B:
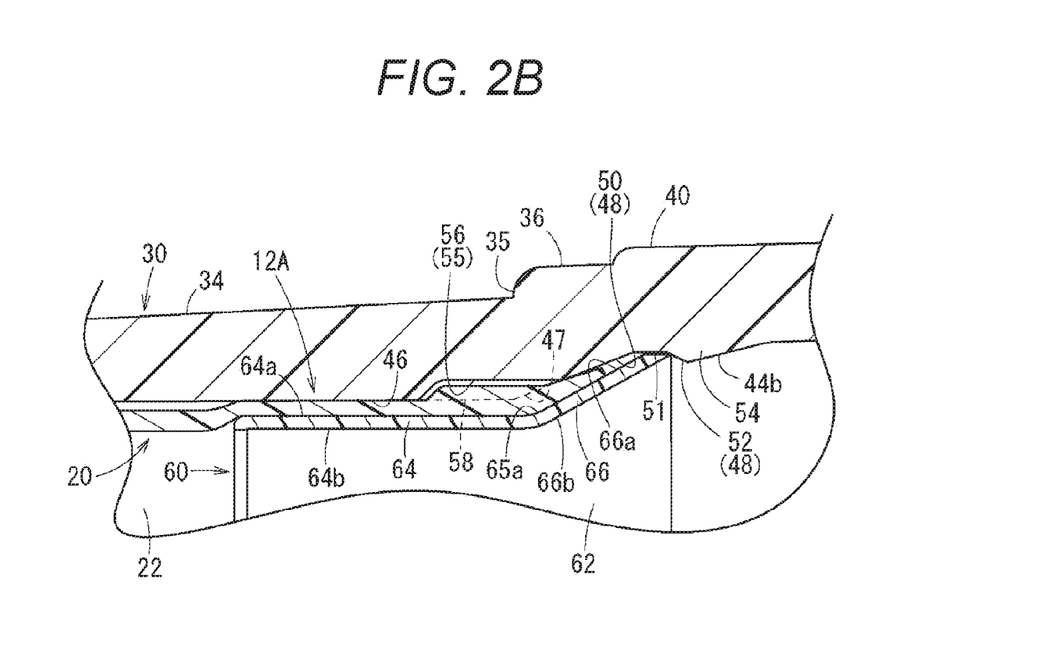
FIG. 2B is an enlarged cross-sectional side view of a catheter body clamped by and between the catheter hub and a securing member of the catheter of FIG. 1.

On the other hand, the securing member 60 is formed into a substantially cylindrical shape having a size small enough to be accommodated in the distal space 42 of the catheter hub 30 and internally includes a hollow portion 62 communicating with the lumen 22 of the catheter body 20. When stored in the catheter hub 30, the securing member 60 includes a distal cylindrical portion 64 disposed to the distal inner peripheral surface 46 in the axial direction of the catheter body 20 and a proximal conical portion 66 disposed next to the recessed inner peripheral surface 48. The securing member 60 may have a thickness (e.g., a wall thickness) that is formed substantially constant in dimension.

The distal cylindrical portion 64 includes a cylindrical portion outer peripheral surface 64a (distal outer peripheral surface) having an outer diameter slightly larger than the diameter of the lumen 22 of the catheter body 20 before assembly. A cylindrical portion inner peripheral surface 64b constituting the hollow portion 62 in the distal cylindrical portion 64 also axially extends with a constant inner diameter in conformance with the cylindrical portion outer peripheral surface 64a. For example, the cylindrical portion inner peripheral surface 64b preferably has an inner diameter designed to be substantially the same as the diameter of the lumen 22 positioned distally from the securing member 60, in a state where the catheter body 20 is secured to the catheter hub 30.

The proximal conical portion 66 includes a conical portion outer peripheral surface 66a (tapered outer peripheral surface) and a conical portion inner peripheral surface 66b which extend from a proximal end of the distal cylindrical portion 64 and have a diameter gradually increasing radially outwardly toward a proximal end (e.g., of the catheter 10A, etc.). The proximal conical portion 66 is formed to have an inclination angle slightly larger than that of the distal tapered inner peripheral surface 50 so that the proximal conical portion 66 has a length matching the axial length from the inner peripheral surface boundary portion 47 to the bottom portion 51 of the catheter hub 30 and the most proximal end of the proximal conical portion 66 is caught by the bottom portion 51. When stored in the catheter hub 30, the most proximal end of the proximal conical portion 66 disposed at the bottom portion 51 of the catheter hub 30 is caught (e.g., in contact with) and retained by the projection portion 54, and the proximal movement (coming off) of the securing member 60 is restricted.

The cylindrical portion outer peripheral surface 64a and the conical portion outer peripheral surface 66a are joined to each other at an outer peripheral surface boundary portion 65a. Furthermore, the cylindrical portion outer peripheral surface 64a and the conical portion outer peripheral surface 66a are inserted into the lumen 22 of the catheter body 20 in intimate contact with an inner peripheral surface of the catheter body 20 from the inside. The catheter body 20 slightly expands radially outward at a position in which the distal cylindrical portion 64 is inserted and flares radially outward at a position in which the proximal conical portion 66 is inserted. The catheter body 20 has a portion expanded by the securing member 60, the portion makes contact with the distal inner peripheral surface 46 and the distal tapered inner peripheral surface 50 of the catheter hub 30, and the catheter body 20 is held with a strong compressive force exerted by the catheter hub 30 and securing member 60.

The catheter 10A may be configured as described above, and the functions and effects thereof will be hereinafter described.

In manufacturing the catheter 10A, the catheter body 20, the catheter hub 30, and the securing member 60 are molded separately and assembled to each other. In some embodiments, the assembly may comprise, first, inserting the securing member 60 into the lumen 22 on the proximal end side of the catheter body 20. Thus, the proximal end side of the catheter body 20 increases in size by an amount of the securing member 60 inserted, compared with the distal end side of the catheter body 20.

Then, the assembled catheter body 20 and securing member 60 may be inserted from the proximal end opening 32b of the catheter hub 30. A portion of the catheter body 20 where the securing member 60 is not inserted has an outer diameter slightly smaller than the smallest inner diameter of the distal inner peripheral surface 46 of the catheter hub 30 and passes smoothly through the catheter hub 30. On the other hand, a portion of the catheter body 20 in which the securing member 60 is inserted has an outer diameter larger than the distal inner peripheral surface 46. Therefore, in a case where the catheter body 20 and the securing member 60 are inserted, when the proximal end side of the catheter body 20 reaches the distal space 42 of the catheter hub 30, the inner peripheral surface of the catheter hub 30 and the outer peripheral surface of the securing member 60 compress the catheter body 20 strongly.

As illustrated in FIG. 2B, the catheter body 20 is held radially between the distal inner peripheral surface 46 of the catheter hub 30 and the cylindrical portion outer peripheral surface 64a of the securing member 60, at a position where the insertion of the catheter body 20 ends. Furthermore, the catheter body 20 is obliquely held between the distal tapered inner peripheral surface 50 of the catheter hub 30 and the conical portion outer peripheral surface 66a of the securing member 60. Thus, the catheter body 20 is firmly secured in the catheter hub 30.

Furthermore, for example, in assembly of the catheter body 20 and the securing member 60, the thickness of the catheter body 20 stretching according to the compression of the catheter hub 30 and the securing member 60 enters into a groove portion 56 formed in the catheter hub 30. In particular, a plurality of the protrusions 58 (the distal inner peripheral surface 46 and the distal tapered inner peripheral surface 50) circumferentially adjacent to a groove portion 56 cooperates with the securing member 60 to tightly hold the catheter body 20 therebetween, and the thickness of the catheter body 20 is stretched circumferentially.

Accordingly, for example, even when the thickness of the catheter body 20 increases due to a manufacturing error or the like, the thickness of the catheter body 20 is well deformed or displaced into the groove portion 56. Therefore, a load (repulsive load of compression) on the catheter hub 30 applied from the catheter body 20 reduces, a damage caused by the catheter body 20 is suppressed, and the catheter body 20 is readily assembled. Furthermore, wrinkles tend to be formed (the thickness tends to increase) at the inner peripheral surface boundary portion 47 due to bending of the catheter body 20, but the groove portion 56 formed within a predetermined range over the inner peripheral surface boundary portion 47 satisfactorily guides the thickness of the catheter body 20 to the groove portion 56.

As described above, the catheter 10A (securing mechanism 12A) may include a configuration in which the relief portion 55 is partially provided in the inner peripheral surface of the catheter hub 30, suppressing the influence of a change in thickness of the catheter body 20. That is, even when the thickness of the catheter body 20 is large, the thickness of the catheter body 20 being held between the catheter hub 30 and the securing member 60 is displaced (inserted) into the relief portion 55, reducing a repulsive load applied from the catheter body 20 on the catheter hub 30 or securing member 60. Furthermore, the inner peripheral surface of the catheter hub 30 and the outer peripheral surface of the securing member 60 have a portion where the relief portion 55 is not provided, the portion exerts a strong compressive force on the catheter body 20. Therefore, the catheter 10A satisfactorily secures the catheter body 20 and the catheter hub 30 via the securing member 60.

Since the relief portion 55 is the groove portion 56, the securing mechanism 12A enables smooth insertion of the catheter body 20 and the securing member 60 along the groove portion 56 when the catheter body 20, the catheter hub 30, and the securing member 60 are assembled. Furthermore, the plurality of groove portions 56 provided to surround the axis of the catheter body 20 accommodates a portion of the thickness of the catheter body 20 to an appropriate groove portion 56, equalizing a repulsive load. Stated another way, a portion of material disposed at the end of the catheter body 20 may be caused to displace or deform into the plurality of groove portions 56 when the catheter body 20 and the securing member 60 are inserted into the catheter hub 30. Without this plurality of groove portions 56, the portion of material trapped or clamped between a catheter hub 30 and a securing member 60 would be unable to significantly move in a radial direction (e.g., perpendicular to the axis of the catheter body 20, etc.). As such, compression of the portion of material between the catheter hub 30 and the securing member 60 would exert a repulsive force between the catheter hub 30 and the securing member 60 causing an increase of stress in the joint of the catheter 10A (e.g., in the area of the catheter 10A where the catheter hub 30, the securing member 60, and the catheter body 20 are connected, etc.). However, providing the plurality of groove portions 56 into which the portion of material may be displaced (e.g., allowing the portion of material to move in a radial direction when compressed), among other things, reduces the repulsive force between the catheter hub 30 and the securing member 60 and decreases the overall stress in the joint of the catheter 10A when compared to a joint that does not include the groove portion 56 and/or relief portion 55 described herein. In addition, even when the catheter body 20 has a non-uniform thickness, the thickness of the catheter body 20 can easily expand, deform, or displace into any of the groove portions 56.

In some embodiments, the groove portion 56 (e.g., relief portion 55) may include a distal end located proximally from the distal end of the securing member 60. Thus, the securing mechanism 12A accommodates the thickness of the catheter body 20 near the inner peripheral surface boundary portion 47 and, at the same time, sufficiently tightly holds the catheter body 20 distally from the groove portion 56.

In addition, the catheter 10A according to embodiments of the present disclosure is not limited to the above-described configuration, and examples of catheters 10B to 10F according to other embodiments will be described below. In the following description, the same reference numerals are given to configurations having the same configurations or the same functions as those previously described, and a detailed description thereof will be omitted.

Figure 3A:
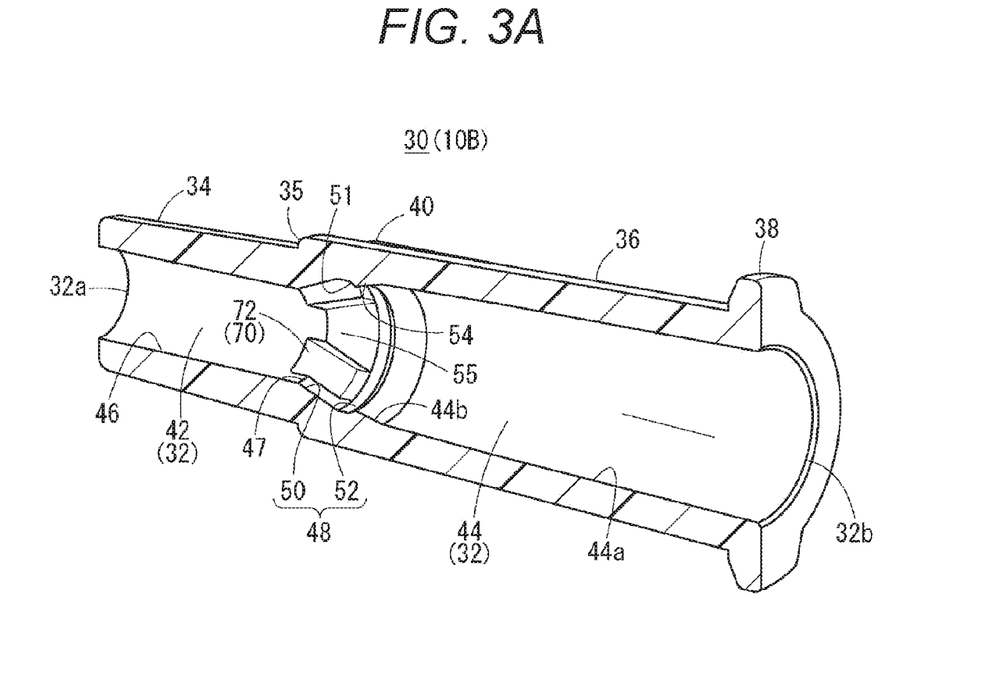
FIG. 3A is a perspective cross-sectional view of a catheter hub of a catheter in accordance with an embodiment of the present disclosure.
Figure 3B:
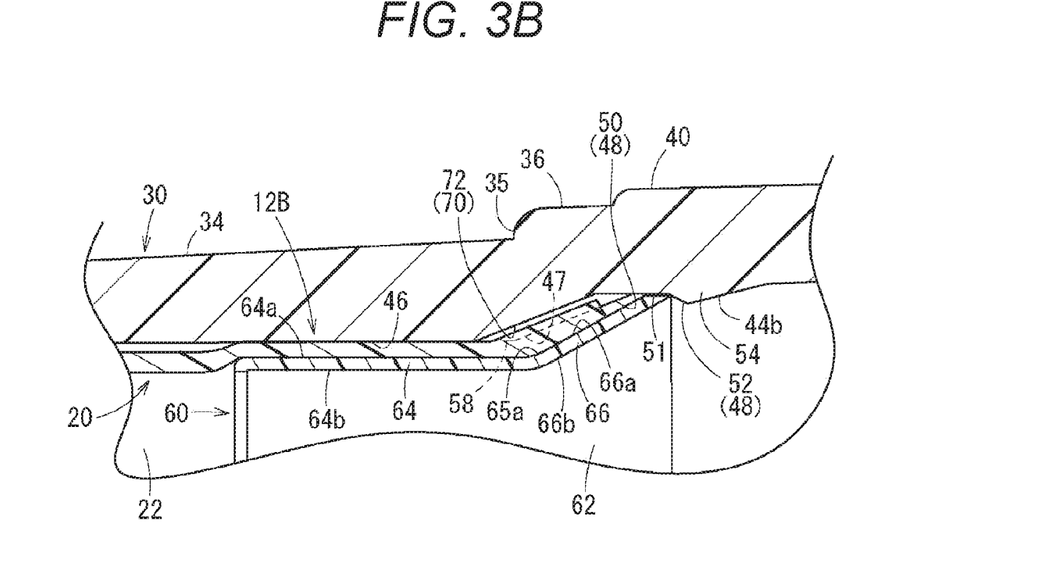
FIG. 3B is an enlarged cross-sectional side view of a catheter body clamped by and between a securing member and the catheter hub of FIG. 3A.

As illustrated in FIGS. 3A and 3B, a catheter 10B according to one embodiment may be slightly different from the catheter 10A previously described, for example, in the shape of a relief portion 70 provided in a securing mechanism 12B.

Specifically, the relief portion 70 may be formed into a groove shape (groove portion 72) which is formed in the inner peripheral surface of the catheter hub 30, similarly to the relief portion 55 described above. A position where a distal end of the groove portion 72 is formed is provided near the inner peripheral surface boundary portion 47 between the distal inner peripheral surface 46 and the distal tapered inner peripheral surface 50 (in the distal inner peripheral surface 46 slightly forward from the inner peripheral surface boundary portion 47). On the other hand, a position where a proximal end of the groove portion 72 is formed is located at the proximal end of the distal tapered inner peripheral surface 50 of the catheter hub 30.

That is, the groove portion 72 may extend in the axial direction of the catheter hub 30, in the distal tapered inner peripheral surface 50. The groove portion 72 may be formed shallow by cutting out (reducing the thickness of) the distal tapered inner peripheral surface 50 and may extend at a constant depth in the distal tapered inner peripheral surface 50.

The catheter 10B may include the relief portion 70 (groove portion 72) described above can provide the same effects as those of the catheter 10A. Particularly, in the catheter 10B, the groove portion 72 may be provided to extend fully in the axial direction of the distal tapered inner peripheral surface 50, and the proximal end of the groove portion 72 may be located proximally from the proximal end of the catheter body 20. Thus, the dimension of the catheter body 20 near the proximal end portion, which relatively easily increases, is readily displaced into the groove portion 72. In other words, even when the thickness of the catheter body 20 near the proximal end portion increases in molding of the catheter body 20, the thickness of the catheter body 20 is displaced into the groove portion 72, and the catheter body 20 and the securing member 60 are readily assembled to the catheter hub 30.

Figure 4A:
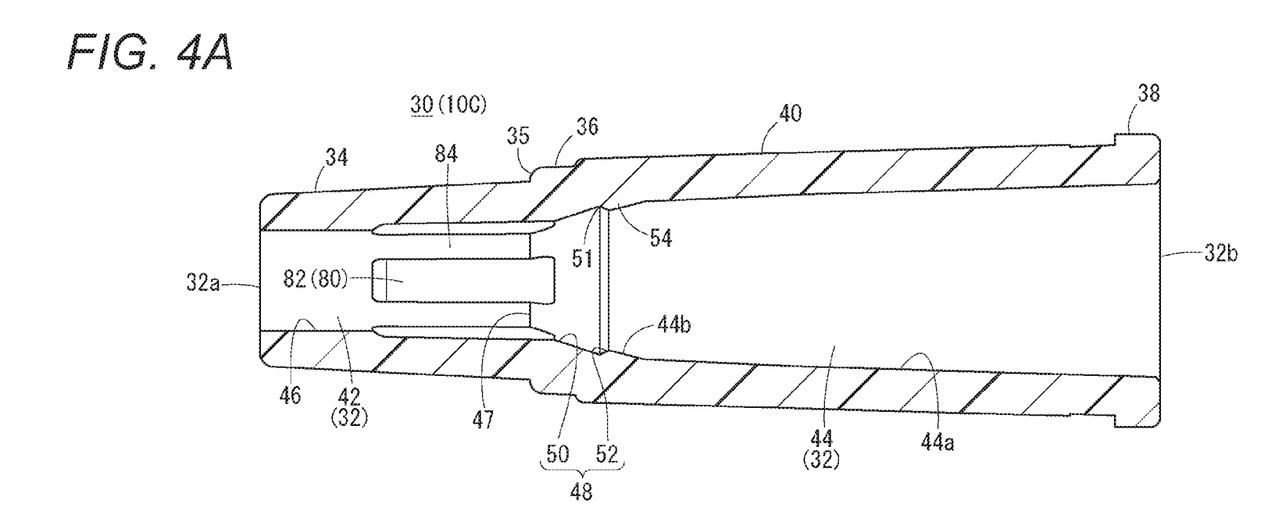
FIG. 4A is a cross-sectional side view of a catheter hub of a catheter in accordance with an embodiment of the present disclosure.
Figure 4B:
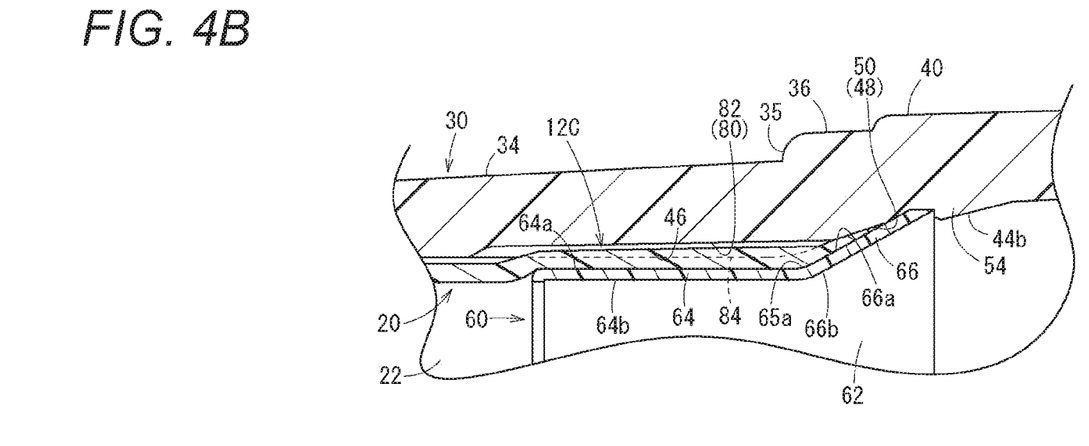
FIG. 4B is an enlarged cross-sectional side view of a catheter body clamped by and between a securing member and the catheter hub of FIG. 4A.

As illustrated in FIGS. 4A and 4B, a catheter 10C according to another embodiment may be slightly different from the catheters 10A and 10B described above, for example, in the shape of a relief portion 80 provided in a securing mechanism 12C.

Specifically, the relief portion 80 may be formed into a groove shape (groove portion 82) which is formed in the inner peripheral surface of the catheter hub 30, similarly to the relief portion 55 described above. A position where a distal end of the groove portion 82 is formed is located forward from an intermediate position in the axial direction of the distal inner peripheral surface 46 of the catheter hub 30 and further distally from the distal end of the securing member 60 stored in the catheter hub 30. The position where the proximal end of the groove portion 82 is formed is the same as that of the groove portion 56 according to the first embodiment.

That is, the groove portion 82 may extend relatively long in the distal inner peripheral surface 46 (longer than the groove portion 56 described above). Furthermore, a space between groove portions 82 circumferentially adjacent to each other may be provided with a protrusion 84 (e.g., a rib) constituted by the distal inner peripheral surface 46 extending long axially and the distal tapered inner peripheral surface 50.

The catheter 10C illustrated in FIGS. 4A and 4B may include the relief portion 80 (groove portion 82) described above and can provide the same effects as those of the catheter 10A. Particularly, in the catheter 10C, since the entire length of a portion facing the cylindrical portion outer peripheral surface 64a of the securing member 60 is defined as the groove portion 82, the securing member 60 near the distal end cooperates with the catheter hub 30 to suppress a compressive force exerted to the catheter body 20. In addition, the groove portion 82 and the protrusion 84 are configured to guide an insertion direction of the catheter body 20, making it possible to further readily assemble the catheter body 20 and the securing member 60 to the catheter hub 30. Furthermore, in the catheter 10C, the thickness of the catheter body 20 near the proximal end side may be formed thick in advance, and the proximal end side of the catheter body 20 may be positively inserted into the groove portion 82 to form a further rigid assembly.

Figure 5A:
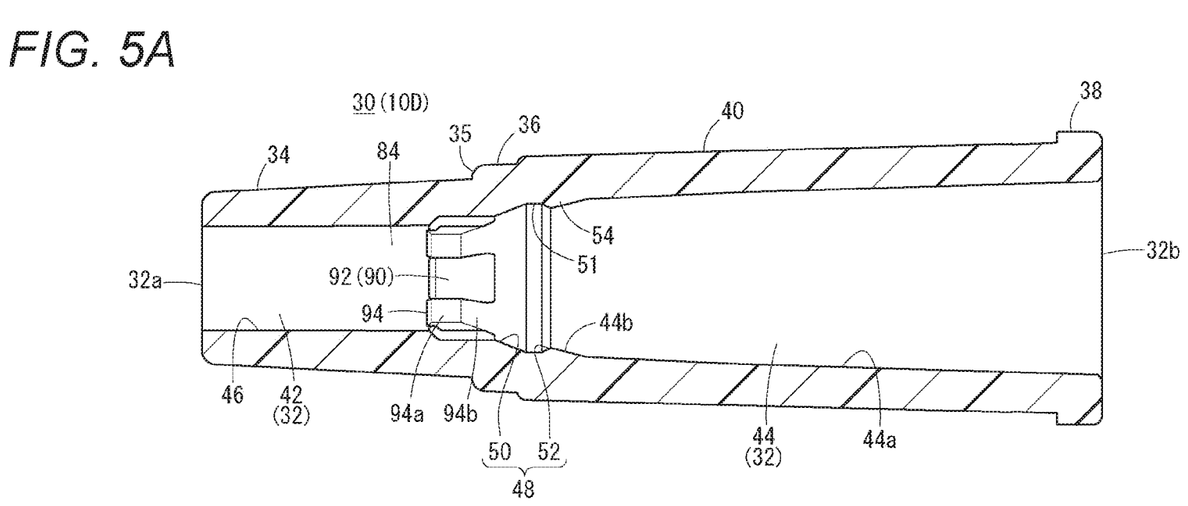
FIG. 5A is a cross-sectional side view of a catheter hub of a catheter in accordance with an embodiment of the present disclosure.
Figure 5B:
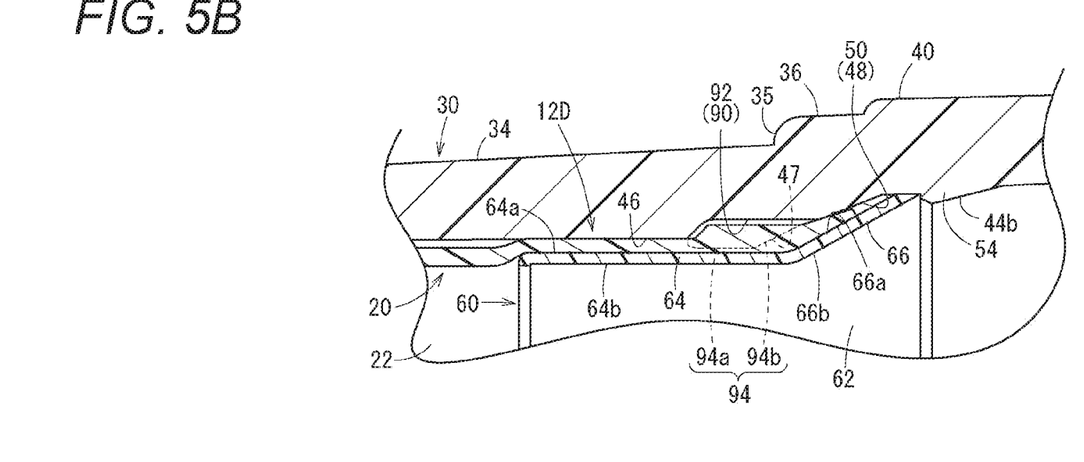
FIG. 5B is an enlarged cross-sectional side view of a catheter body clamped by and between a securing member and the catheter hub of FIG. 5A.

As illustrated in FIGS. 5A and 5B, a catheter 10D (securing mechanism 12D) according to one embodiment may be slightly different from the catheters 10A to 10C described above, for example, in that a protruding portion 94 may be provided at a circumferentially adjacent position of a relief portion 90 (groove portion 92).

Specifically, in the securing mechanism 12D, the groove portions 92 and the protruding portions 94 may be alternately formed circumferentially at positions across the inner peripheral surface boundary portion 47 between the distal inner peripheral surface 46 and the distal tapered inner peripheral surface 50. Each groove portion 92 is formed at the same depth as that of the groove portion 56 according to the first embodiment, with the distal inner peripheral surface 46 as a reference surface.

On the other hand, each protruding portion 94 projects radially inward (toward the distal space 42) in a direction opposite to the groove portion 92, with the distal inner peripheral surface 46 as a reference surface. The protruding portion 94 includes a protruding surface 94a which is formed in a flat shape, and a proximal end side of the protruding portion 94 is defined as an inclined surface 94b which is bent from the protruding surface 94a and continuously extending to the distal tapered inner peripheral surface 50. For example, the protruding portion 94 preferably has an amount of protrusion designed to be approximately the same as an amount of recess of the groove portion 92 with the distal inner peripheral surface 46 as the reference surface.

The catheter 10D of FIGS. 5A and 5B may include the groove portion 92 and the protruding portion 94 described above and further tightly hold the catheter body 20 at the protruding portion 94 and fully accommodates the thickness of the catheter body 20 stretched from the protruding portion 94 to the groove portion 92.

Figure 6A:
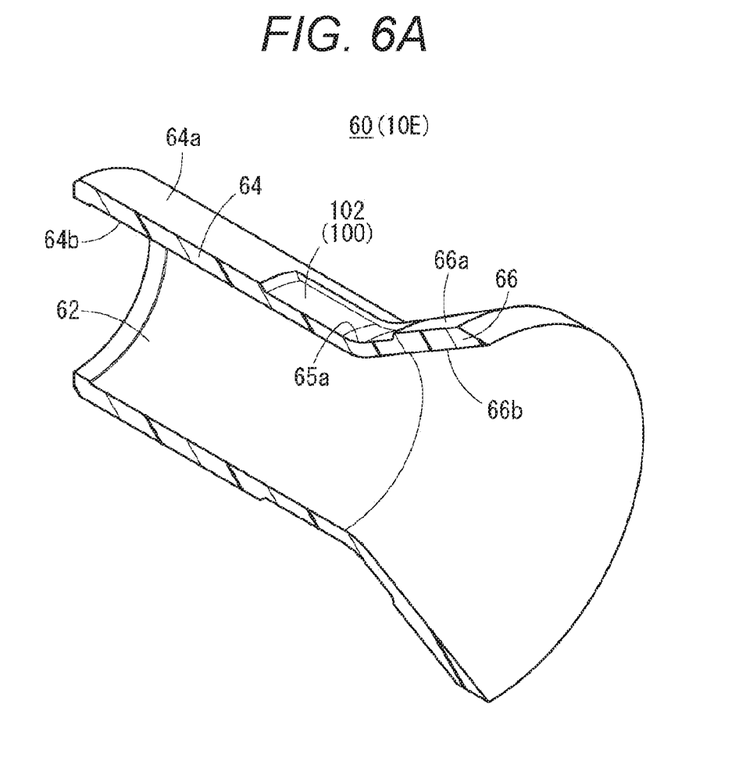
FIG. 6A is a perspective cross-sectional view of a securing member of a catheter in accordance with an embodiment of the present disclosure
Figure 6B:
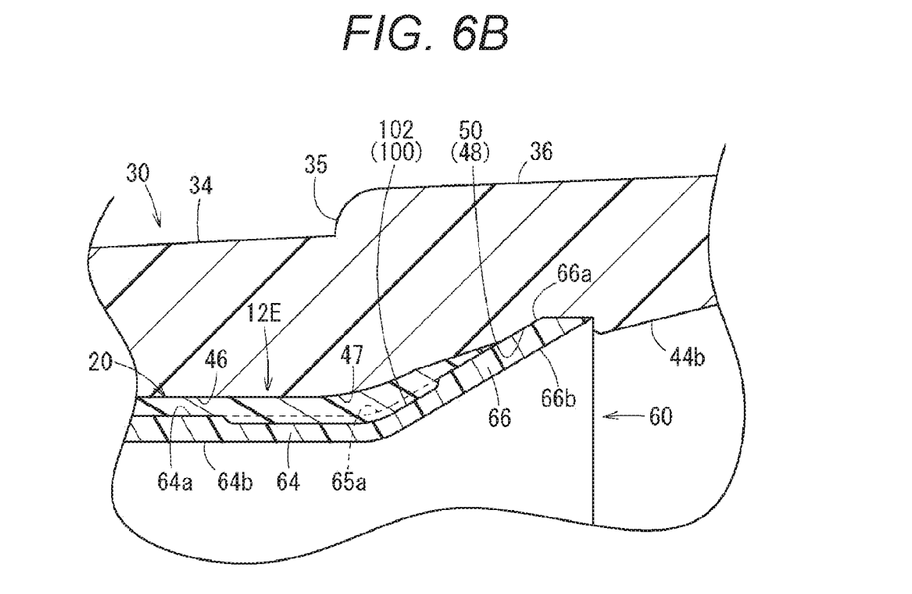
FIG. 6B is an enlarged cross-sectional side view of a catheter body clamped by and between a catheter hub and the securing member of FIG. 6A.

As illustrated in FIGS. 6A and 6B, a catheter 10E (securing mechanism 12E) according to another embodiment may be different from the catheters 10A to 10D described above, for example, in that a relief portion 100 (groove portion 102) may be provided in the securing member 60. In addition, owing to the groove portion 102 provided in the securing member 60, in the inner peripheral surface of the catheter hub 30, the distal inner peripheral surface 46 and the distal tapered inner peripheral surface 50 may be formed to smoothly continue at the inner peripheral surface boundary portion 47.

In the securing member 60, a plurality of the groove portions 102 may be provided across the outer peripheral surface boundary portion 65a between the cylindrical portion outer peripheral surface 64a and the conical portion outer peripheral surface 66a, in the circumferential direction of the securing member 60. Each groove portion 102 may be formed shallow and provided not to reach the distal end of the distal cylindrical portion 64 and the proximal end of the proximal conical portion 66. Thus, the securing member 60 can sufficiently maintain the strength of the securing member 60 itself and can tightly hold the catheter body 20 in cooperation with the catheter hub 30.

As described above, the catheter 10E (securing mechanism 12E) in which the groove portion 102 is provided in the securing member 60 can also provide the same effects as those of the catheter 10A described above. In particular, the groove portion 102 can be readily provided in the outer peripheral surface of the securing member 60 to improve manufacturing efficiency as a whole of the catheter 10E. In short, the relief portions 55, 70, 80, 90, and 100 according to the present disclosure may be provided on either the catheter hub 30 or the securing member 60 or, although not illustrated, both of the catheter hub 30 and the securing member 60.

Figure 7A:
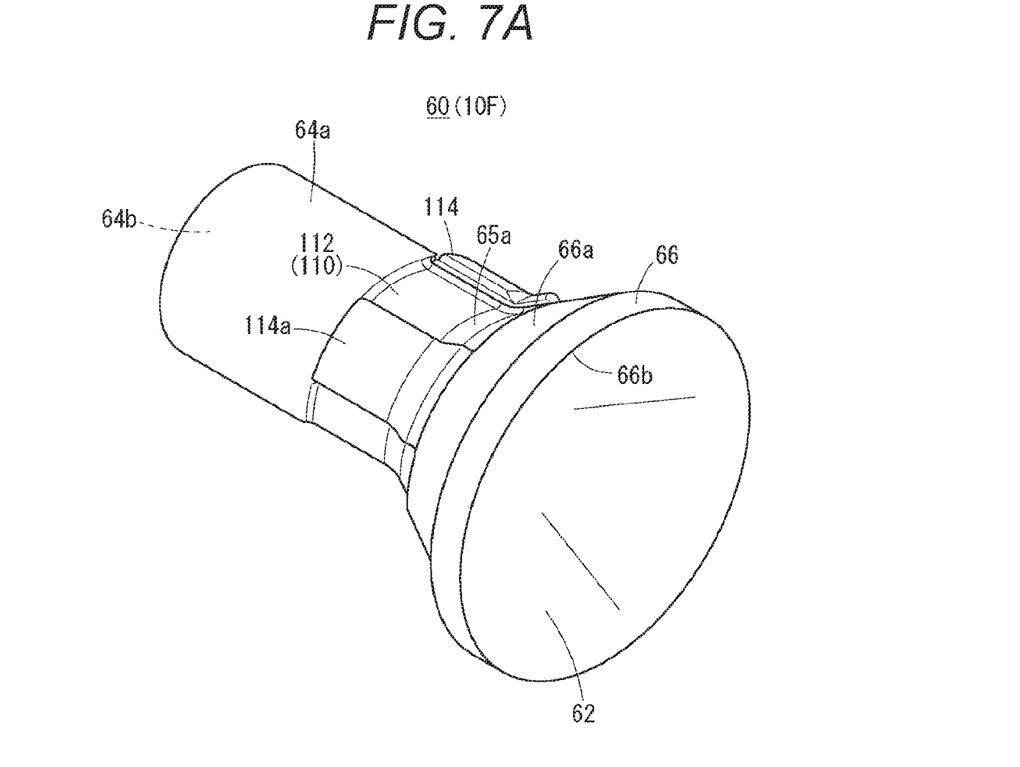
FIG. 7A is a perspective cross-sectional view of a securing member of a catheter in accordance with an embodiment of the present disclosure.
Figure 7B:
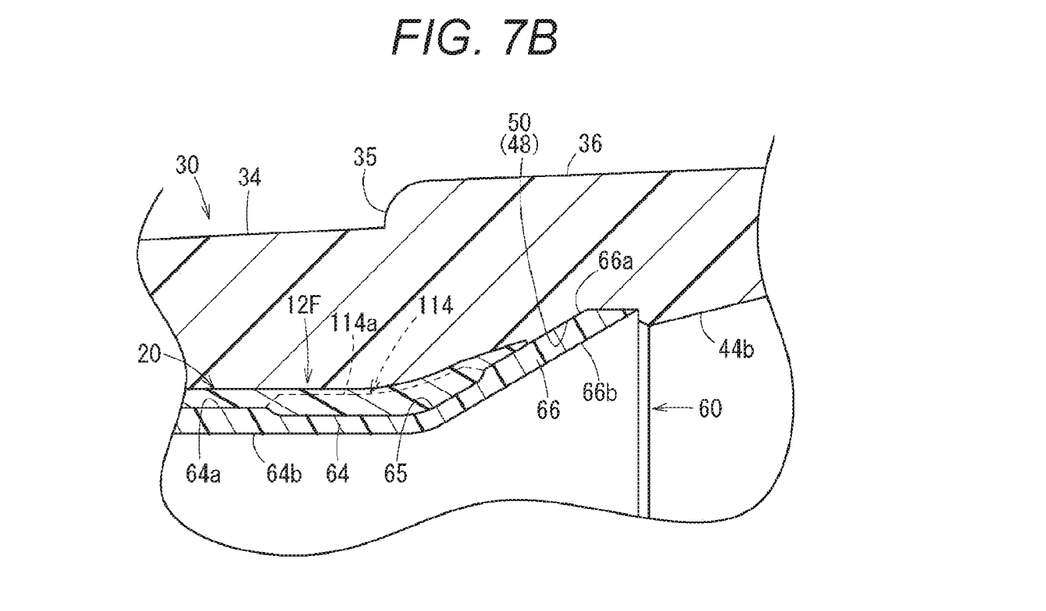
FIG. 7B is an enlarged cross-sectional side view of a catheter body clamped by and between a catheter hub and the securing member of FIG. 7A.

As illustrated in FIGS. 7A and 7B, a catheter 10F (securing mechanism 12F) according to an embodiment of the present disclosure may be different from the catheters 10A to 10E described above, for example, in that a relief portion 110 (groove portion 112) and a protruding portion 114 may be provided in the securing member 60. That is, a portion around the outer peripheral surface boundary portion 65a between the cylindrical portion outer peripheral surface 64a and the conical portion outer peripheral surface 66a of the securing member 60 may be formed to have recessed and protruded shapes circumferentially.

For example, the groove portion 112 may have the same configuration as that described in conjunction with FIGS. 6A and 6B. On the other hand, the protruding portion 114 is protruded radially outwardly (in a direction opposite to the groove portion 112) with a small height, with the cylindrical portion outer peripheral surface 64a and the conical portion outer peripheral surface 66a as reference surfaces, and has a protruding surface 114a formed into a flat shape.

In the catheter 10F described above, the protruding portion 114 of the securing member 60 cooperates with the catheter hub 30 to tightly hold the catheter body 20, while the thickness of the catheter body 20 expands into, or is satisfactorily accommodated by, the groove portion 112 of the securing member 60. In addition, the protruding portion 114 may function as a rib for reinforcing the shape of the securing member 60.

It should be noted that the embodiments of the present disclosure are not limited to the above-described embodiments, and various modifications may be made within the spirit and scope of the disclosure. For example, the relief portions 55, 70, 80, 90, 100, and 110 may not be formed in a groove shape axially extending in the inner peripheral surface of the catheter hub 30 or the outer peripheral surface of the securing member 60. As other examples, a configuration in which one or more annular grooves are provided in a direction orthogonal to the axial direction, a configuration in which small recessed dots (dimples) are provided, a configuration in which one or more helical grooves are provided, and the like may be adopted.

What is claimed is:

1. A catheter, comprising:
   a catheter body;
   a hollow catheter hub configured to receive insertion of the catheter body;
   a securing member disposed in the catheter hub to hold the catheter body between the securing member and the catheter hub, the securing member having an outer peripheral surface making a close contact with an inner peripheral surface of the catheter body, and
   a recessed relief portion into which a thickness of the catheter body enters, the relief portion comprising a groove portion partially provided circumferentially in an inner peripheral surface of the catheter hub.

2. The catheter according to claim 1, wherein
   the groove portion comprises a plurality of groove portions arranged circumferentially and separated from one another surrounding an axis of the catheter body.

3. The catheter according to claim 1, wherein
   the inner peripheral surface of the catheter hub includes a distal inner peripheral surface having a continuous constant inner diameter and a tapered inner peripheral surface extending from a proximal end of the distal inner peripheral surface and having an inner diameter gradually increasing proximally, and
   the relief portion is provided across an inner peripheral surface boundary portion between the distal inner peripheral surface and the tapered inner peripheral surface.

4. The catheter according to claim 3, wherein
   a distal end of the relief portion is located proximally from a distal end of the securing member.

5. The catheter according to claim 3, wherein
   a distal end of the relief portion is located distally from a distal end of the securing member.

6. The catheter according to claim 3, wherein
   a proximal end of the relief portion is located proximally from a proximal end of the catheter body.

7. The catheter according to claim 3, wherein
   a distal end of the relief portion is provided proximally from a distal end of a distal outer peripheral surface of the securing member, and a proximal end of the relief portion is provided distally from a proximal end of a tapered outer peripheral surface.

8. The catheter according to claim 1, wherein
   in the outer peripheral surface of the securing member, a protruding portion protruding in a direction opposite to the relief portion is formed at a position circumferentially adjacent to the relief portion.

9. The catheter according to claim 1, wherein the groove portion extends in an axial direction of the catheter hub, and wherein the groove portion comprises a plurality of grooves arranged circumferentially and separated from one another surrounding an axis of the catheter body.

10. A catheter, comprising:
    a catheter body;
    a hollow catheter hub configured to receive insertion of the catheter body;
    a securing member disposed in the catheter hub to hold the catheter body between the securing member and the catheter hub, the securing member having an outer peripheral surface making a close contact with an inner peripheral surface of the catheter body, and
    a groove portion cut out to extend in an axial direction into which a thickness of the catheter body enters, the groove portion being partially provided circumferentially in an inner peripheral surface of the catheter hub.

11. The catheter according to claim 10, wherein
the groove portion comprises a plurality of groove portions arranged circumferentially surrounding an axis of the catheter.

12. The catheter according to claim 11, wherein the inner peripheral surface of the catheter hub comprises a distal inner peripheral surface having a continuous constant inner diameter and a tapered inner peripheral surface extending from a proximal end of the distal inner peripheral surface and having an inner diameter gradually increasing proximally.

13. The catheter according to claim 12, wherein the catheter hub comprises a projection portion disposed at a location of the catheter distal to the tapered inner peripheral surface and proximal to the distal inner peripheral surface, and wherein the projection portion comprises a diameter less than any diameter of the tapered inner peripheral surface.

14. The catheter according to claim 13, wherein a distal outer peripheral surface of the securing member is disposed in a proximal end of the catheter body, and wherein the securing member is restricted from moving proximally relative to the catheter hub by a proximal most end of the securing member contacting the projection portion of the catheter hub.

15. The catheter according to claim 14, wherein a diameter of the distal outer peripheral surface of the securing member is greater than an inner diameter of the catheter body at the proximal end of the catheter body.

16. The catheter according to claim 15, wherein a diameter of a distal inner peripheral surface of the securing member is substantially similar to the inner diameter of the catheter body.

17. A catheter, comprising:
a catheter hub having a proximal end and a distal end disposed opposite the proximal end, wherein the catheter hub is hollow from the proximal end to the distal end and comprises an inner surface;
a catheter body having a lumen;
a securing member inserted into the lumen at an end of the catheter body, wherein the securing member flares the end of the catheter body outwardly from a center of the lumen at a proximal end of the securing member, and wherein the securing member is disposed entirely inside the catheter hub and is restricted from axial movement by a ridge in contact with the securing member disposed proximal to the flared end of the catheter body; and
a relief portion into which a thickness of the catheter body is displaced and accommodated, wherein the relief portion comprises a plurality of grooves disposed around an axis of the catheter, wherein the relief portion is disposed the inner surface of the catheter hub.

18. The catheter according to claim 17, wherein the catheter hub comprises an inner peripheral surface comprising a distal inner peripheral surface having a continuous constant inner diameter and a tapered inner peripheral surface extending from a proximal end of the distal inner peripheral surface and having an inner diameter gradually increasing proximally, and wherein the ridge comprises a projection having a diameter less than any diameter of the tapered inner peripheral surface.

19. The catheter according to claim 18, wherein a diameter of a distal outer peripheral surface of the securing member inserted into the end of the catheter body is greater than an inner diameter of the catheter body lumen.

20. The catheter according to claim 19, wherein the flared end of the catheter body is clamped by and between the securing member and the catheter hub, and wherein movement of the catheter body relative to the hub is restricted by the thickness of the catheter body displaced into and accommodated by the relief portion.

* * * * *